(12) United States Patent
McLaren et al.

(10) Patent No.: US 7,608,230 B2
(45) Date of Patent: Oct. 27, 2009

(54) SAMPLE CONDITIONING SYSTEM FOR REMOVING SELENIUM FROM A GAS STREAM

(75) Inventors: Scott E. McLaren, Centennial, CO (US); Kevin M. Fisher, Highlands Ranch, CO (US)

(73) Assignee: Apogee Scientific, Inc, Englewood, CO (US)

( * ) Notice: Subject to any disclaimer, the term of this patent is extended or adjusted under 35 U.S.C. 154(b) by 376 days.

(21) Appl. No.: 11/471,108

(22) Filed: Jun. 19, 2006

(65) Prior Publication Data

US 2007/0292327 A1    Dec. 20, 2007

(51) Int. Cl.
*B01D 47/00*    (2006.01)

(52) U.S. Cl. .................... 423/210; 423/212; 423/213.7; 423/99; 423/509

(58) Field of Classification Search .................. None
See application file for complete search history.

(56) References Cited

U.S. PATENT DOCUMENTS

| 1,711,742 A * | 5/1929 | Nordlander .................. 436/81 |
| 6,790,420 B2 * | 9/2004 | Breen et al. ............... 423/215.5 |
| 2004/0062697 A1 * | 4/2004 | Mortson et al. ............. 423/235 |

* cited by examiner

*Primary Examiner*—Melvin C Mayes
*Assistant Examiner*—Melissa Stalder
(74) *Attorney, Agent, or Firm*—Dorr, Carson & Birney, P.C.

(57) ABSTRACT

A sample conditioning system removes selenium from a flue gas sample to provide more accurate measure of mercury in the gas stream. Ammonia or another basic reagent is added to the sampled gas stream to increase the pH of the condensate, and thereby ensuring the removal of hydrogen selenide.

9 Claims, 1 Drawing Sheet

SAMPLE CONDITIONING SYSTEM FOR REMOVING SELENIUM FROM A GAS STREAM

BACKGROUND OF THE INVENTION

1. Field of the Invention

The present invention relates generally to the field of systems for measuring pollutants in a gas stream. More specifically, the present invention discloses a sample conditioning system modification for removing selenium to enable more accurate measurements of mercury in the gas stream.

2. Statement of the Problem

Selenium is a trace constituent present in the flue gas from some combustion sources, such as coal-fired electric power plants. Selenium is typically present as elemental selenium or selenium dioxide ($SeO_2$). The presence of selenium or selenium compounds can interfere with the accurate measurement of other pollutants (e.g., mercury) in the gas stream.

Mercury is also a trace constituent present in some flue gas streams. The mercury is typically present as elemental mercury or in an oxidized state (e.g., $HgCl_2$ or $HgO$). Prior to measuring the mercury concentration, the sampled gas stream is first processed in some conventional manner to chemically reduce all of the oxidized mercury to elemental mercury. For example, one approach has been to add propane or other reducing agents to the flue gas stream, which consume available oxygen and other oxidizing agents. The result is a reductive environment capable of catalytically reducing chemical compounds found in the gas stream. The mercury concentration in this processed gas stream is then analyzed using cold vapor atomic absorbance (CVAA) or other conventional techniques that are specific for elemental mercury.

It has been observed that at some sites, the tubing downstream from the catalyst quickly becomes fouled and removes mercury from the gas stream. The distinct garlic smell of hydrogen selenide ($H_2Se$) can be detected in the fouled tubing. Laboratory testing confirms that hydrogen selenide can react with elemental mercury to form mercuric selenide, which will not be detected by the CVAA detector.

Thus, a problem arises in the reduction step in that at least a portion of the selenium compounds in the gas steam will also be reduced to hydrogen selenide. Hydrogen selenide can react with mercury to form mercuric selenide (HgSe), thus interfering with the mercury measurement.

Solution to the Problem. The present invention seeks to eliminate this interference by scrubbing the gas exiting the mercury reduction unit with a basic aqueous solution to remove hydrogen selenide from the processed gas stream. Hydrogen selenide is a weak acid that is less soluble in acidic solutions. In particular, acid gases (e.g., HCl) present in the flue gas can lower the pH of the scrubbing solution to a point where the hydrogen selenide is no longer soluble to a significant degree.

To improve the solubility of hydrogen selenide, ammonia or another basic reagent can be injected into the gas stream prior to the condenser to increase the pH of the scrubbing solution and improve the removal of hydrogen selenide.

SUMMARY OF THE INVENTION

This invention provides a sample conditioning systems to remove selenium from a flue gas stream to provide more accurate measure of mercury in the gas stream. Ammonia or another basic reagent is added to the sampled gas stream to increase the pH of the condensate, and thereby ensuring the removal of hydrogen selenide.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Figure 1:
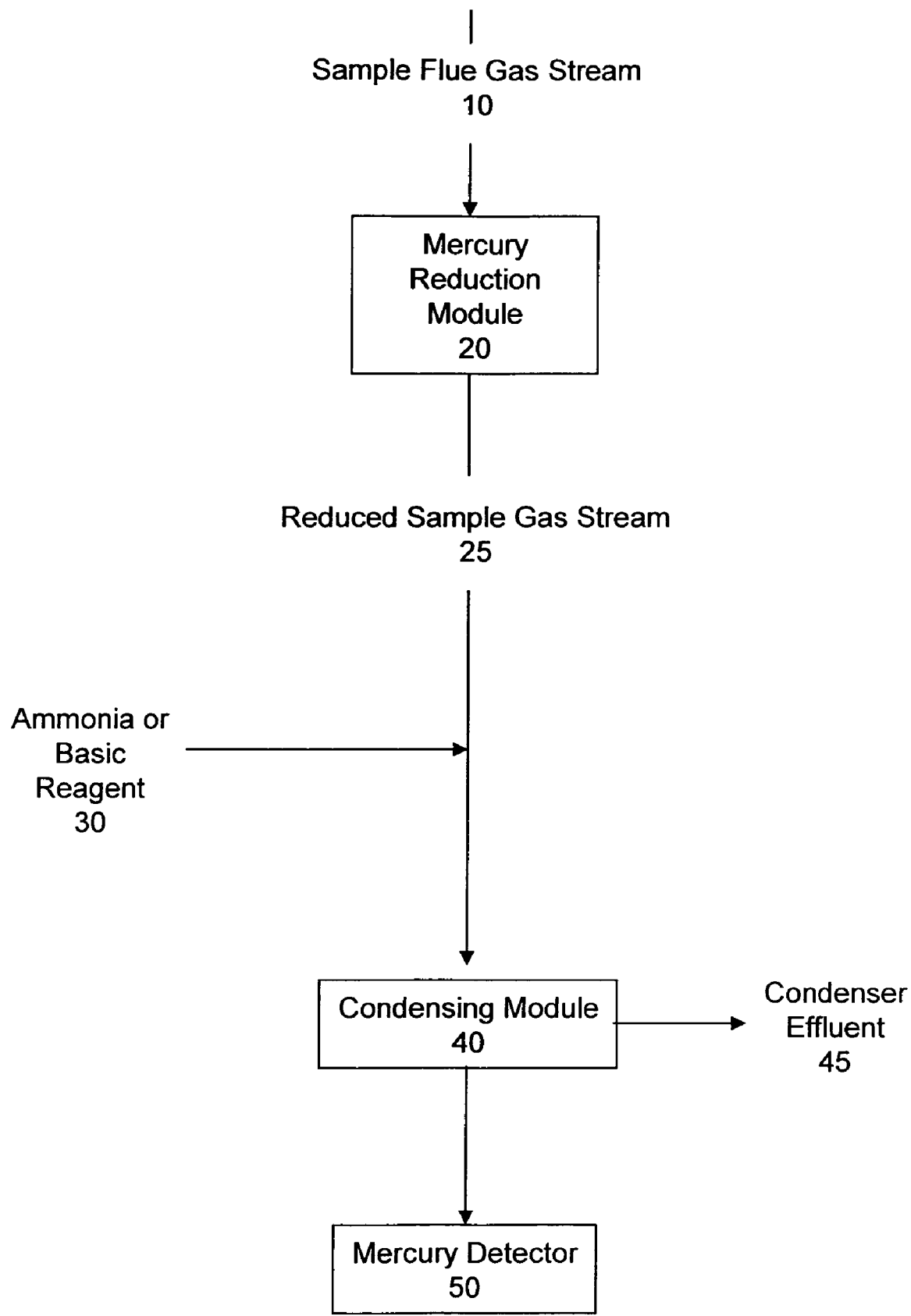
FIG. 1 is a schematic block diagram of the present invention.

Turning to FIG. 1, a schematic block diagram is provided of the present invention. A sample flue gas stream 10 containing selenium, selenium compounds, sulfur and/or sulfur compounds is drawn into the system and passes through a mercury reduction module 20, which converts oxidized forms of mercury in the sample gas to elemental mercury. For example, propane or other reducing agents can be added to the sample flue gas stream 10, which consume available oxygen and other oxidizing agents. The result is a reductive environment capable of catalytically reducing chemical compounds found in the gas stream. The resulting reduced sample gas stream 25 also has been found to typically contain hydrogen selenide, hydrogen sulfide and other reduced compounds.

Ammonia or another basic reagent 30 is injected into the reduced sample gas stream 25 to increase its pH. For example, gas-phase ammonia can be injected through a number of injectors at the outlet of the reduction module 20. The gas stream then enters a condensing module 40 or scrubber that removes moisture, condensibles, and soluble gases. The increased pH of the sample gas stream enables the condensing module 40 to remove virtually all of the hydrogen selenide present in the sample gas stream. In addition to hydrogen selenide, the resulting condenser effluent 45 also typically contains hydrogen sulfide and other soluble compounds. However, elemental mercury is not soluble in water, and therefore remains in the gas stream. The scrubbed gas stream is then processed by a mercury detector 50 (e.g., a CVAA detector) to measure elemental mercury.

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

We claim:

1. A method for conditioning a flue gas stream to remove selenium prior to measuring mercury in the gas stream, said method comprising:

adding a basic reagent to the gas stream to increase solubility of hydrogen selenide in water; and removing moisture and soluble gases, including hydrogen selenide, from the gas stream.

2. The method of claim 1 wherein the basic reagent comprises ammonia.

3. The method of claim 1 further comprising adding a reducing agent to the gas stream to consume available oxidizing agents in the gas stream.

4. The method of claim 3 wherein the reducing agent comprises propane.

5. The method of claim 1 wherein moisture and soluble gases are removed from the gas stream by a condenser.

6. A method for measuring mercury in a flue gas stream comprising:
   adding a reducing agent to the gas stream to consume available oxidizing agents in the gas stream and convert oxidized forms of mercury in the gas stream to elemental mercury;
   adding a basic reagent to the gas stream to increase solubility of hydrogen selenide in water;
   removing moisture and soluble gases, including hydrogen selenide, from the gas stream; and
   measuring elemental mercury in the gas stream.

7. The method of claim 6 wherein the basic reagent comprises ammonia.

8. The method of claim 6 wherein the reducing agent comprises propane.

9. The method of claim 6 wherein moisture and soluble gases are removed from the gas stream by a condenser.

* * * * *